United States Patent
Einberger et al.

(10) Patent No.: US 9,066,189 B2
(45) Date of Patent: Jun. 23, 2015

(54) NON-PRESSURE SENSITIVE IMPLANTABLE MICROPHONE

(71) Applicant: MED-EL Elektromedizinische Geraete GmbH, Innsbruck (AT)

(72) Inventors: Tobias Einberger, Inssbruck (AT); Josef Baumgartner, Ranggen (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 120 days.

(21) Appl. No.: 13/868,197

(22) Filed: Apr. 23, 2013

(65) Prior Publication Data

US 2013/0289655 A1    Oct. 31, 2013

Related U.S. Application Data

(60) Provisional application No. 61/638,644, filed on Apr. 26, 2012.

(51) Int. Cl.
*A61N 1/04* (2006.01)
*H04R 25/00* (2006.01)
*A61N 1/36* (2006.01)

(52) U.S. Cl.
CPC .......... *H04R 25/606* (2013.01); *A61N 1/36032* (2013.01); *H04R 2225/67* (2013.01)

(58) Field of Classification Search
CPC . A61N 1/36032; A61N 1/0541; H04R 25/606
USPC ........................ 607/55, 56, 57, 137
See application file for complete search history.

(56) References Cited

U.S. PATENT DOCUMENTS

| | | | |
|---|---|---|---|
| 2,803,129 A | 8/1957 | Bradfield | 73/610 |
| 5,772,575 A * | 6/1998 | Lesinski et al. | 600/25 |
| 5,977,689 A * | 11/1999 | Neukermans | 310/324 |
| 6,093,144 A | 7/2000 | Jaeger et al. | 600/25 |
| 6,636,768 B1 | 10/2003 | Harrison | 607/57 |
| 7,481,761 B2 | 1/2009 | Blau et al. | 600/25 |
| 7,722,524 B2 * | 5/2010 | Lupin et al. | 600/25 |
| 7,860,259 B2 | 12/2010 | Onishi et al. | 381/190 |
| 2001/0003788 A1 | 6/2001 | Ball et al. | 600/25 |
| 2004/0039245 A1 | 2/2004 | Jaeger et al. | 600/25 |

(Continued)

FOREIGN PATENT DOCUMENTS

EP    1747699 B1    7/2014 ............ H04R 25/00

OTHER PUBLICATIONS

International Searching Authority, International Search Report and Written Opinion, PCT/US13/37689, date of mailing Sep. 13, 2013, 23 pages.

*Primary Examiner* — Christopher D Koharski
*Assistant Examiner* — Michael Carey
(74) *Attorney, Agent, or Firm* — Sunstein Kann Murphy & Timbers LLP

(57) ABSTRACT

An implantable microphone is described for use in hearing prosthesis systems. A cylindrical microphone housing has opposing circular cylinder ends and an interior volume containing an incompressible housing liquid. At least one housing membrane is on one of the cylinder ends and is in contact with the housing liquid and moveable in response to an acoustic signal outside the housing. An acoustic-electric transducer is coupled to the housing membrane for converting movement of the housing membrane into a corresponding electrical microphone signal.

12 Claims, 3 Drawing Sheets

(56) References Cited

U.S. PATENT DOCUMENTS

| | | | |
|---|---|---|---|
| 2005/0020873 A1 | 1/2005 | Berrang et al. | 600/25 |
| 2005/0137447 A1 | 6/2005 | Bernhard | 600/25 |
| 2005/0245990 A1 | 11/2005 | Roberson | 607/507 |
| 2009/0022353 A1* | 1/2009 | Goldstein et al. | 381/380 |
| 2009/0034773 A1 | 2/2009 | Song | 381/369 |
| 2009/0043149 A1 | 2/2009 | Abel | 600/25 |
| 2011/0137109 A1 | 6/2011 | Zahnert et al. | 600/25 |
| 2011/0144415 A1 | 6/2011 | Hellmuth et al. | 600/25 |

* cited by examiner

NON-PRESSURE SENSITIVE IMPLANTABLE MICROPHONE

This application claims priority from U.S. Provisional Application 61/638,644, filed Apr. 26, 2012, which is incorporated herein by reference.

TECHNICAL FIELD

The present invention relates to an implantable microphone for a hearing prosthesis system such as a cochlear implant system.

BACKGROUND ART

A normal ear transmits sounds as shown in FIG. 1 through the outer ear 101 to the tympanic membrane 102 which moves the bones of the middle ear 103 that vibrate the oval window opening of the cochlea 104. The cochlea 104 is a long narrow duct that is wound spirally about a central axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ear's ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system. An external microphone provides an audio signal input to an external signal processor 111 where various signal processing schemes can be implemented. The processed signal is then converted into a digital data format such as a sequence of data frames for transmission into an implanted stimulator 108. Besides receiving the processed audio information, the implanted stimulator 108 may also perform additional signal processing such as error correction, pulse formation, etc. and produces stimulation signals (based on the extracted audio information) that are sent through an electrode lead 109 to an implanted electrode array 112. The electrode array 112 includes multiple electrode contacts 110 on its surface that deliver the stimulation signals to adjacent neural tissue of the cochlea 104 which the brain interprets as sound. The individual electrode contacts 110 may be activated sequentially, or simultaneously in one or more groups of electrode contacts 110.

Though existing commercial products generally use an external microphone to sense the acoustic environment, there would be an advantage to an implantable microphone. Among other things, an implantable microphone needs to be hermetically sealed from the environment of the adjacent tissue. This makes implantable microphones very sensitive to pressure changes such as those that occur on an airplane flight. For high acoustic sensitivity, a good acoustic impedance match to the surrounding tissue is necessary, which due to the required hermeticity is achieved using thin metal membranes. Pressure changes on the outside of the microphone relative to the hermetic inside of the microphone then can cause a deformation of the membrane, which produces bad microphone characteristics or even a total microphone failure. This problem can be mitigated somewhat by increasing the pressure inside the hermetic microphone housing and thus shifting the pressure range. But the change with pressure in the microphone characteristics remains unsolved.

SUMMARY

Embodiments of the present invention are directed to an implantable microphone for use in hearing prosthesis systems. A cylindrical microphone housing has opposing circular cylinder ends and an interior volume containing an incompressible housing liquid. At least one housing membrane is on one of the cylinder ends and is in contact with the housing liquid and moveable in response to an acoustic signal outside the housing. An acoustic-electric transducer is coupled to the housing membrane for converting movement of the housing membrane into a corresponding electrical microphone signal.

Embodiments of the present invention also are directed to an implantable microphone for use in hearing prosthesis systems. A microphone housing has a double cone shape with opposing circular cone ends and an interior volume containing an incompressible housing liquid, wherein the double cone shape is narrower in the middle and wider towards the ends. At least one housing membrane is on one of the cone ends that is in contact with the housing liquid and moveable in response to an acoustic signal outside the housing. An acoustic-electric transducer is coupled to the housing membrane for converting movement of the housing membrane into a corresponding electrical microphone signal.

In further specific embodiments, there may be housing membranes on each cylinder end, with an acoustic-electric transducer coupled to each housing membrane. There also may be an interior membrane within the interior volume of the microphone housing between the at least one housing membrane and the acoustic-electric transducer for coupling the movement of the housing membrane to the acoustic-electric transducer. In some such embodiments, there may be a bypass tube hat provides a fluid passage across the interior membrane. There may also be a microphone signal module for developing the microphone signal and coupling the microphone signal as an electrical output from the microphone housing. For example, the microphone signal module may be located in the incompressible liquid within the interior volume. And there may be an attachment pad located on the outer surface of the microphone housing for connecting the microphone housing to adjacent bone in the implanted patient.

Embodiments of the present invention also include an implantable hearing prosthesis system having an implantable microphone according to any of the foregoing. For example, the implantable hearing prosthesis system may be a cochlear implant system.

DETAILED DESCRIPTION

Various embodiments of the present invention are directed to an implantable microphone with improved handling of pressure changes. The interior volume of the microphone is filled with an incompressible liquid. The use of an incompressible liquid results in the microphone being uninfluenced by pressure changes.

Figure 1:
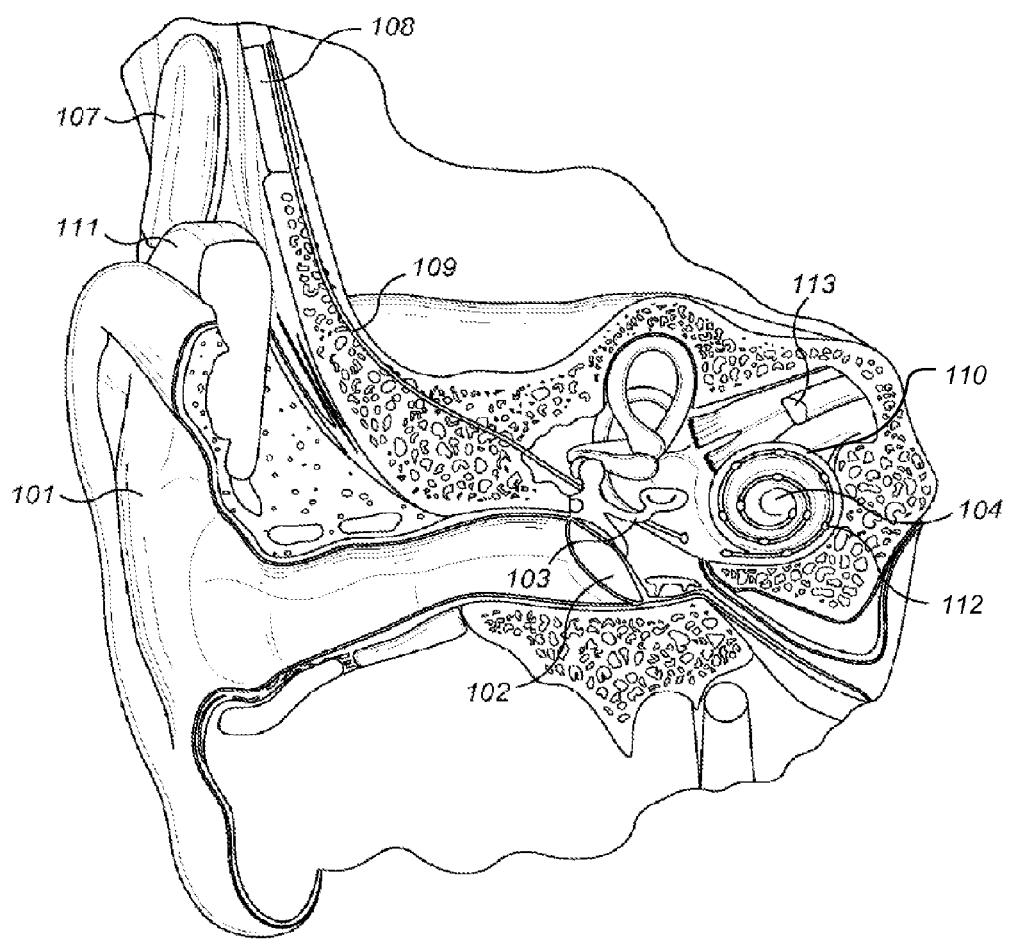
FIG. 1 shows various anatomical structures in a normal human ear and various elements of a typical cochlear implant system.
Figure 2:
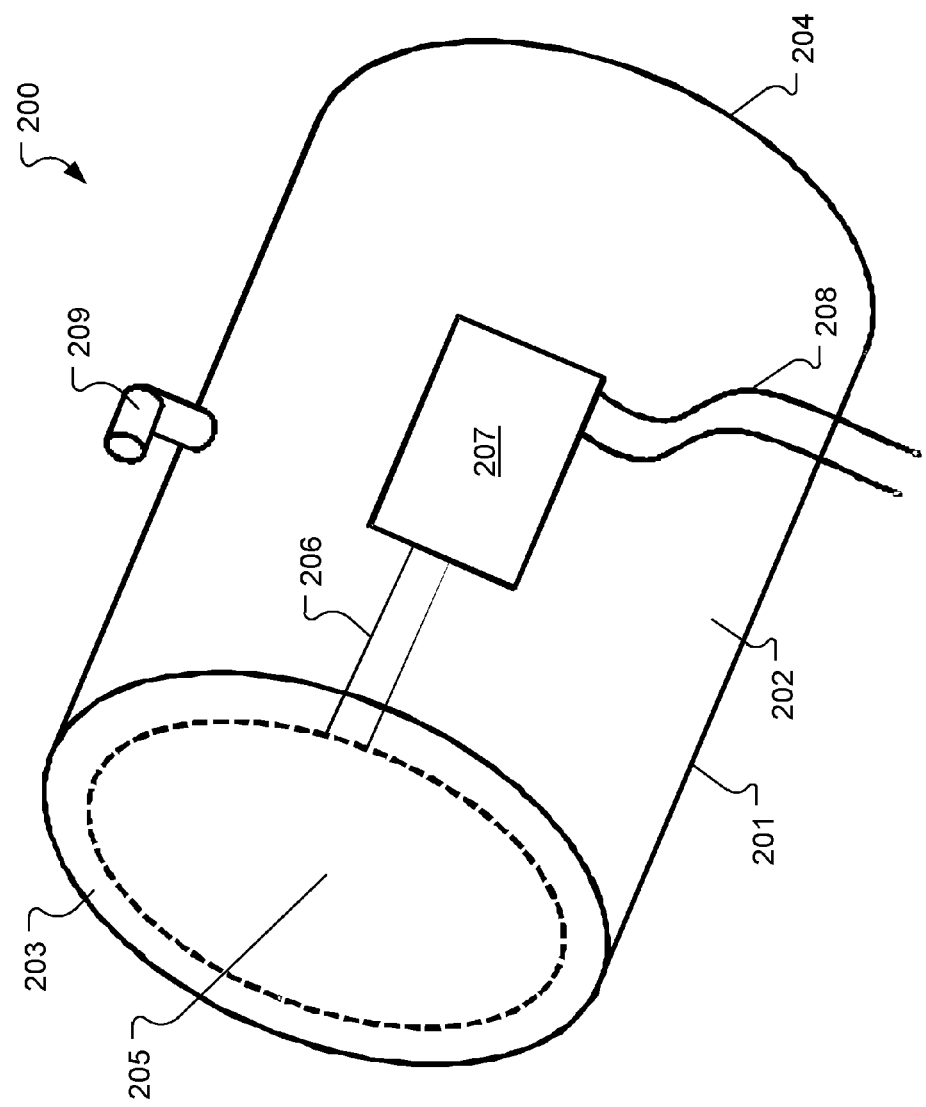
FIG. 2 shows an example of an implantable microphone according to one specific embodiment of the present invention.

FIG. 2 shows one specific embodiment of such an implantable microphone 200 for use in hearing prosthesis systems. A cylindrical microphone housing 201 has an interior volume 202 that contains an incompressible housing liquid such as an oil, silicone-based fluid, or a fluid dispersion (water-based or not). There are housing membranes 203 and 204 at either cylindrical end of the microphone housing 201 which are in contact with the housing liquid. The housing membranes 203 and 204 are moveable in response to an acoustic signal outside the microphone housing 201.

An acoustic-electric transducer 205 is coupled to one or both of the housing membranes 203 or 204 for converting the acoustic generated movement of the housing membrane into a corresponding electrical microphone signal. Using two opposing housing membranes 203 and 204 helps provide a good acoustic impedance match to the surrounding tissue and enables the acoustic wave to travel through the liquid-filled interior volume 201 of the microphone 200. The acoustic-electric transducer 205 may be a piezo element attached to one of the housing membranes 203 and/or 204, but some other kind of acoustic-electric transducer 205 also can be used. In some embodiments, there may be an acoustic-electric transducer 205 on each of the housing membranes 203 and 204 whose signals may be summed together in an advantageous way.

The output sensing signal of the acoustic-electric transducer 205 may be coupled by one or more transducer wires 206 to a microphone signal module 207 with the microphone housing 201 to perform signal conditioning/pre-processing of the transducer sensing signal. Depending on the specific properties of the housing liquid (e.g. if the liquid is electrically conductive) a microphone sensing module 207 may be encapsulated in protective material or enclosed in its own module housing within the interior volume 202. The processed microphone output signal from the microphone sensing module 207 is coupled out from the microphone 200 by one or more microphone output wires 208 (e.g., to an implanted stimulator 108 for further signal processing, etc.).

Figure 3:
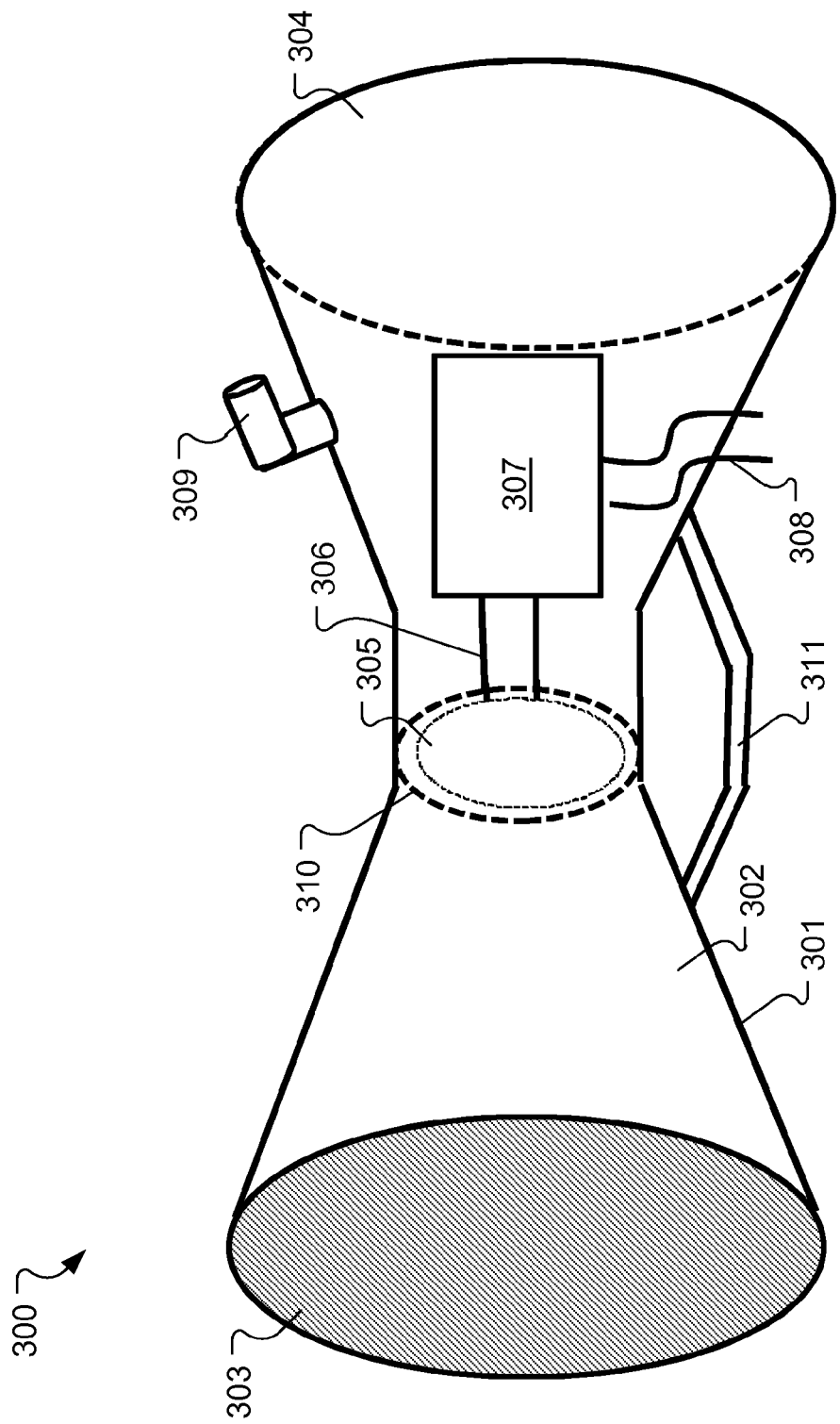
FIG. 3 shows another example of an implantable microphone according to another specific embodiment of the present invention.

FIG. 3 shows another example of another implantable microphone 300 in which the microphone housing 301 has a double cone shape which is narrower in the middle and wider towards the opposing circular cone ends. The microphone housing 301 has an interior volume 302 that contains an incompressible housing liquid that results in the desired improvement in response to exterior pressure changes. There are housing membranes 303 and 304 located at the cone ends of the microphone housing 301.

In the embodiment shown in FIG. 3, an interior intermediate membrane 310 is located within the interior volume 302 of the microphone housing 301 with an acoustic-electric transducer 305 mounted thereto. Due to the double cone shape of the microphone housing 301, the outer housing membranes 303 and 304 are larger than the intermediate membrane 310 which results in amplification of the acoustic signal sensed by the acoustic-electric transducer 305 at the intermediate membrane 310. The intermediate membrane 310 can be optimized to meet the specific needs of the acoustic-electric transducer 305 (e.g. non-conductive), while the outer end housing membranes 303 and 304 can be optimized to best ensure hermeticity and impedance matching. The interior intermediate membrane 310 also protected against mechanical impact.

The use of an intermediate membrane 310 could result in an undesirable pre-load which could alter the microphone characteristic. Thus, the microphone 300 shown in FIG. 3 has a bypass tube 311 that provides a fluid passage across the intermediate membrane 305. Another fluid bypass option is to provide a small hole in the intermediate membrane 310 to avoid a pre-load.

Microphone signal module 307 is located in the incompressible liquid within the interior volume 301 and receives the transducer sensing signal from the acoustic-electric transducer 305 via one or more transducer wires 306 and produces an output microphone signal that is coupled by one or more microphone output wires 308 as an electrical output from the microphone housing 301.

Relative movement is needed between the microphone housing and the microphone to develop a sensing signal. Thus in general the mass of the microphone housing should be larger than the mass of the incompressible liquid within the interior volume of the microphone housing, or else the microphone housing should be securely fixed to a large mass such as the skull bone. Thus some embodiments of an implantable microphone may include an attachment pad in between the housing membrane and the bone site that provides a good acoustic impedance match. Due to the tapered middle part, the double cone-shaped microphone 300 has the advantage that the mass of the interior liquid is reduced compared to the cylinder shaped microphone 200. Additionally the tissue between the cones effectively increases the mass of the housing.

Embodiments of an implantable microphone containing an incompressible liquid thus are less sensitive to changes in pressure than conventional microphones. In addition, there is an improved acoustic impedance match since the acoustic impedance of the liquid is closer to the impedance of the surrounding tissue as compared to air. But for a condenser microphone or electret microphone, the higher permittivity of a liquid compared to air may reduce the acoustic-electric transducer factor, so a liquid with low permittivity should be used. Moreover, the interior liquid should be compatible to the transducer material and to possible electronics within the microphone.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable microphone for use in hearing prosthesis systems, the microphone comprising:
    a cylindrical microphone housing with opposing circular cylinder ends and having an interior volume containing an incompressible housing liquid;
    at least one housing membrane on one of the cylinder ends that is in contact with the housing liquid and moveable in response to an acoustic signal outside the housing;

an acoustic-electric transducer coupled to the at least one housing membrane for converting movement of the housing membrane into a corresponding electrical microphone signal;

an interior membrane within the interior volume of the microphone housing between the at least one housing membrane and the acoustic-electric transducer for coupling the movement of the housing membrane to the acoustic-electric transducer; and a bypass tube providing a fluid passage across the interior membrane.

2. An implantable microphone according to claim 1, wherein there are housing membranes on each cylinder end, and wherein an acoustic-electric transducer is coupled to each housing membrane.

3. An implantable microphone according to claim 1, further comprising:

a microphone signal module for developing the microphone signal and coupling the microphone signal as an electrical output from the microphone housing.

4. An implantable microphone according to claim 3, wherein the microphone signal module is located in the incompressible liquid within the interior volume.

5. An implantable microphone according to claim 1, further comprising:

an attachment pad located on the outer surface of the microphone housing for connecting the microphone housing to adjacent bone in the implanted patient.

6. An implantable hearing prosthesis system having an implantable microphone according to any of claims 1, 2 and 3-5.

7. An implantable microphone for use in hearing prosthesis systems, the microphone comprising:

a microphone housing having a double cone shape with opposing circular cone ends and having an interior volume containing an incompressible housing liquid, wherein the double cone shape is narrower in the middle and wider towards the ends;

at least one housing membrane on one of the cone ends that is in contact with the housing liquid and moveable in response to an acoustic signal outside the housing;

an acoustic-electric transducer coupled to the at least one housing membrane for converting movement of the housing membrane into a corresponding electrical microphone signal;

an interior membrane within the interior volume of the microphone housing between the at least one housing membrane and the acoustic-electric transducer for coupling the movement of the housing membrane to the acoustic-electric transducer; and a bypass tube providing a fluid passage across the interior membrane.

8. An implantable microphone according to claim 7, wherein there are housing membranes on each cone end, and wherein an acoustic-electric transducer is coupled to each housing membrane.

9. An implantable microphone according to claim 7, further comprising:

a microphone signal module for developing the microphone signal and coupling the microphone signal as an electrical output from the microphone housing.

10. An implantable microphone according to claim 9, wherein the microphone signal module is located in the incompressible liquid within the interior volume.

11. An implantable microphone according to claim 7, further comprising:

an attachment pad located on the outer surface of the microphone housing for connecting the microphone housing to adjacent bone in the implanted patient.

12. An implantable hearing prosthesis system having an implantable microphone according to any of claims 7, 8 and 9-11.

* * * * *